(12) United States Patent
Pohjonen et al.

(10) Patent No.: US 7,041,107 B2
(45) Date of Patent: May 9, 2006

(54) INSTRUMENT

(75) Inventors: Timo Pohjonen, Tampere (FI); Auvo Kaikkonen, Tampere (FI); Jan Nieuwenhuis, Gorinchem (NL); Pia Ahvenjärvi, Tampere (FI); Olli Karhi, Oulu (FI); Timo Reunamäki, Tampere (FI); Jukka Koljonen, Nokia (FI)

(73) Assignee: Inion Ltd., Tampere (FI)

( * ) Notice: Subject to any disclaimer, the term of this patent is extended or adjusted under 35 U.S.C. 154(b) by 233 days.

(21) Appl. No.: 10/420,363

(22) Filed: Apr. 22, 2003

(65) Prior Publication Data
US 2004/0092950 A1    May 13, 2004

(30) Foreign Application Priority Data
Apr. 22, 2002    (FI)    .................... 20020771

(51) Int. Cl.
*A61B 17/00*    (2006.01)

(52) U.S. Cl. ...................................... 606/84

(58) Field of Classification Search .............. 606/80, 606/84, 81, 82, 79, 83, 85; 30/366, 358
See application file for complete search history.

(56) References Cited

U.S. PATENT DOCUMENTS

| | | | | |
|---|---|---|---|---|
| 2,250,434 | A * | 7/1941 | Dugaw | 7/158 |
| 5,190,548 | A * | 3/1993 | Davis | 606/80 |
| 5,437,675 | A * | 8/1995 | Wilson | 606/80 |
| 6,030,406 | A * | 2/2000 | Davis et al. | 606/198 |
| 6,258,093 | B1 * | 7/2001 | Edwards et al. | 606/80 |
| 6,270,501 | B1 * | 8/2001 | Freiberg et al. | 606/79 |
| 6,383,188 | B1 * | 5/2002 | Kuslich et al. | 606/80 |
| 6,416,517 | B1 * | 7/2002 | Harder et al. | 606/80 |
| 6,783,533 | B1 * | 8/2004 | Green et al. | 606/80 |

FOREIGN PATENT DOCUMENTS

WO    WO 01/60268    8/2001

* cited by examiner

*Primary Examiner*—Pedro Philogene
(74) *Attorney, Agent, or Firm*—Banner & Witcoff, Ltd.

(57) ABSTRACT

An instrument for shaping a mouth part of a drilled tunnel provided in a bone. The instrument includes a shaft having a longitudinal axis and a first and a second end. The first end of the shaft is provided with a projection, which includes a blade for shaping the mouth part of the drilled tunnel when the instrument is turned around the longitudinal axis of the shaft. The instrument is asymmetric at an intersecting surface perpendicular to the longitudinal axis and intersecting with the blade, the instrument thus shaping the surfaces surrounding the first end only substantially within an area corresponding with a turning angle of such a turning movement.

11 Claims, 2 Drawing Sheets

INSTRUMENT

FIELD OF THE INVENTION

The invention relates to an instrument for shaping a mouth part of a drilled tunnel provided in a bone, the instrument including a shaft having a longitudinal axis and a first and a second end, the first end of the shaft being provided with a projection, which includes a blade for shaping the mouth part of the drilled tunnel when the instrument is turned around the longitudinal axis of the shaft.

BACKGROUND OF THE INVENTION

Numerous surgical procedures are known wherein connective tissue damaged due to an accident or a disease is repaired and/or replaced. In some of such procedures, tunnels are drilled into a bone, and tissue grafts or artificial grafts are inserted into these tunnels. In the reconstruction of an anterior cruciate ligament (ACL) or a posterior cruciate ligament (PCL), for example, either a soft tissue graft or a bone-tendon-bone graft is fixed to the tunnels drilled into ends of femora and tibiae. In most cases the graft is fixed into a drilled tunnel by a screw, which is typically screwed between the graft and the drilled tunnel, pressing and locking the graft against the wall of the drilled tunnel.

Conventionally, the screws fixing the graft have been manufactured from biostable materials, such as metal. Increasingly often, however, such screws are manufactured from materials that are absorbed into the body, i.e. biodegradable materials. The use of such screws in surgical procedures is constantly on the increase since they provide a considerable advantage over conventional implants manufactured from metal: they do not have to be removed from the body after the operated tissue has healed. This enables an operation to remove the implant to be avoided, which is naturally advantageous in terms of patient satisfaction and resource load as well as costs.

Screws manufactured from biodegradable materials allow for less angular force than metallic screws do. In order to prevent a biodegradable screw from breaking down while being screwed into a drilled tunnel, the mouth part of the drilled tunnel is enlarged e.g. by bevelling the edge of the mouth part. Different instruments have been developed for the purpose, and they are usually called notchers. Hereinafter, in the present application the term instrument is used for referring to instruments used for shaping a mouth part of a drilled tunnel.

Instruments are known which are used for shaping a mouth part by turning the instrument at the mouth part of a drilled tunnel. Such an instrument includes several blades arranged radially around the shaft of the instrument. When the operator turns the instrument at the mouth of the drilled tunnel by a wrist movement, the turning angle being about 90° at its largest, the blades shape the surfaces surrounding the instrument everywhere. Such a shaped surface thus extends 360° around the instrument.

Operators usually wish to perform an operation such that a graft is first inserted into a drilled tunnel and the mouth part of the drilled tunnel is shaped using an instrument only thereafter. The instrument is then inserted into the mouth part of the drilled tunnel, between the wall of the drilled tunnel and the graft. The mouth part of the drilled tunnel now being shaped, the blades may damage the graft. The problem is particularly apparent when a soft tissue graft is used. The blades may damage the graft even to the extent that it no longer can be used in the operation but has to be replaced by a new one.

BRIEF DESCRIPTION OF THE INVENTION

An object of the present invention is to provide a novel and improved instrument for shaping a mouth part of drilled tunnels.

The instrument of the invention is characterized in that the instrument is asymmetric at an intersecting surface perpendicular to the longitudinal axis and intersecting with the blade, and that the instrument shapes the surfaces surrounding the first end only substantially within an area corresponding with a turning angle of such a turning movement.

The idea underlying the invention is that the bone-shaping blades of the instrument are arranged asymmetrically such that they shape the bone only substantially within the area covered by the turning angle of the instrument.

An advantage of the invention is that the instrument substantially reduces the risk of damaging a graft inserted into a drilled tunnel.

The idea underlying an embodiment of the invention is that an expander part insertable into the drilled tunnel is provided between the tip of the first end of the instrument and the blade. The expander part expands the space between a graft and a wall of the drilled tunnel, packing the bone tighter. An instrument provided with a blade to shape the mouth part of a drilled tunnel and an expander part reduces the number of devices necessitated by an operation.

The idea underlying another embodiment of the invention is that the shaft of the instrument is provided with a cannula to enable a control spike to be inserted therethrough. An advantage of this embodiment is that by inserting such a control spike between a graft and a wall of the drilled tunnel prior to inserting the instrument into the drilled tunnel, the mouth part of the drilled tunnel can be shaped precisely at a correct point since the control spike prevents the instrument from becoming inclined or otherwise disadvantageously positioned. After the mouth part of the drilled tunnel has been shaped, the instrument can be removed from the drilled tunnel while the control spike can be left in its place between the wall of the drilled tunnel and the graft in order to wait for installation of a screw or another fixing element taking place next, utilizing the control spike.

In an embodiment of the invention, the opening for the control spike in the instrument, i.e. the cannula, also enables a different working order. The operator may first insert the instrument between the drilled tunnel and the graft and, controlled by the cannula in the instrument, position the control spike precisely at the correct place in the drilled tunnel only after the mouth part has been shaped. Surprisingly enough, the cannula in the instrument also enables the number of working phases to be reduced if the instrument and the control spike are inserted simultaneously between the wall of the drilled tunnel and the graft and the control spike has already been inserted into the cannula of the instrument prior to the insertion of the instruments into the drilled tunnel.

BRIEF DESCRIPTION OF THE DRAWINGS

The invention will be described in closer detail in the accompanying drawings, in which.

For the sake of clarity, the figures show the invention in a simplified manner. Like reference numerals identify like elements.

DETAILED DESCRIPTION OF THE INVENTION

Figure 1:
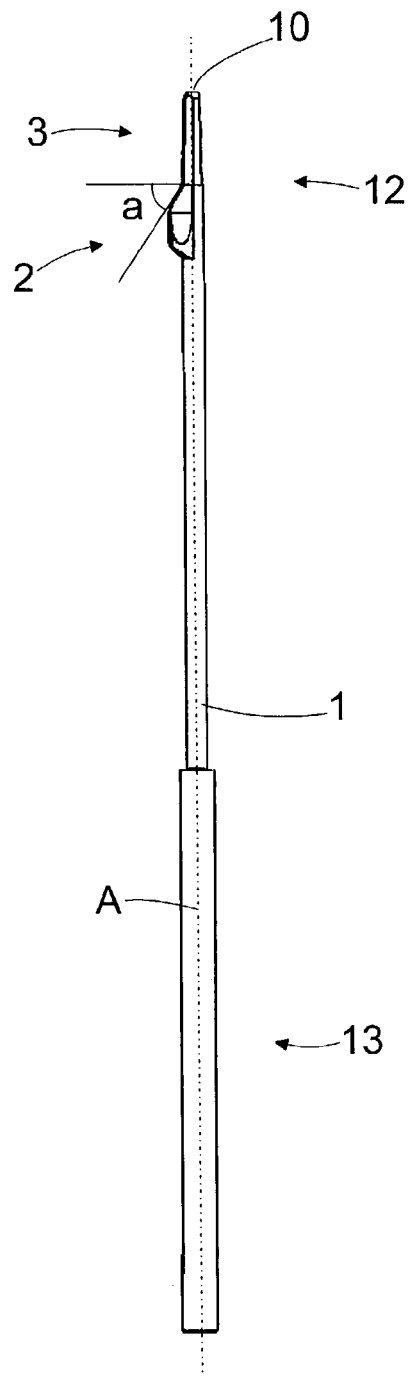
FIG. 1 is a schematic side view showing an instrument of the invention.
Figure 2:
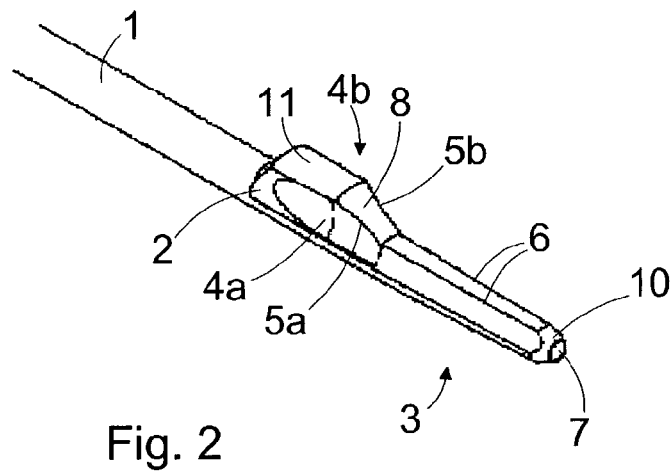
FIG. 2 is a schematic view showing a first end of the instrument shown in FIG. 1.
Figure 3:
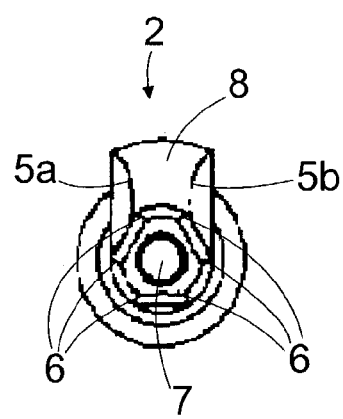
FIG. 3 is a schematic end view showing the instrument shown in FIG. 1 as seen from a direction of the first end.

FIG. 1 is a schematic side view showing an instrument of the invention, FIG. 2 is a schematic view showing a first end of the instrument shown in FIG. 1, and FIG. 3 is a schematic view showing the instrument shown in FIG. 1 as seen from a direction of the first end. The instrument includes a shaft 1 having a first end 12 and a second end 13. The shaft 1 is further provided with a longitudinal axis A. The shaft 1 is manufactured from a sterilizable material, preferably from metal, such as stainless steel. The cross-section of the shaft 1 is circular herein but it may also have another shape. In an operation, the first end 12 of the shaft is inserted into a drilled tunnel. The operator uses the instrument at the second end 13 of the shaft having a handle or a corresponding actuator being arranged therein.

The first end 12 of the shaft is provided with a projection 2 having a blade 4a, 4b arranged on its both sides, substantially in a direction parallel to the longitudinal axis A. The blades 4a, 4b have a concave cutting edge 5a, 5b. The cutting edge 5a, 5b cuts the bone at the mouth part of the drilled tunnel. With respect to the axial direction A, the cutting edges 5a, 5b have a positive cutting angle a, in other words a point of the edge 5a, 5b closer to the shaft 1 is closer to an imaginary plane arranged at a tip 10 of the first end and perpendicular to the longitudinal axis A than a point of the edge 5a, 5b located farther away from the shaft. As seen from an end of the instrument, the blades 4a, 4b are mutually substantially parallel.

Between the cutting edges 5a, 5b there is provided a face 8 which, substantially in an axial direction, continues as a projection top 11 over the projection 2. When necessary, the face 8 and the top 11 can be used for bone packing. Bone packing refers to compressing porous bone by subjecting the bone to pressure, which results in the bone becoming slightly compressed. This increases the strength of a wall of a drilled tunnel. Bone packing also enables the diameter of the drilled tunnel to be enlarged, which makes a screw easier to insert in the drilled tunnel.

The instrument is asymmetric at an intersecting surface perpendicular with respect to the longitudinal axis A and arranged at a blade. When the operator turns the instrument around the longitudinal axis A, the projection 2 and the blades 4a, 4b therewith perform a turning movement equal in size to the angle of the turning movement with respect to the longitudinal axis A. The blades 4a, 4b modify the surfaces surrounding the first end 12 of the instrument only substantially within an area covered by the turning movement.

Immediately at the front of the projection 2 there is provided an expander part 3, which extends all the way to the tip 10 of the first end of the shaft. The expander part 3 is tapered such that its diameter is larger at the part facing the projection 2 than at the part facing the tip 10. The tapering makes the instrument easier to insert into the drilled tunnel. The expander part 3 is further provided with bevels which form a total of six expander part edges 6 in a direction parallel with the longitudinal axis A. The bevels make the instrument easier to insert into the drilled tunnel. The expander part edges 6 enable the bone walls of the drilled tunnel to be modified. The expander part 3 may also be implemented without bevels and edges 6. Furthermore, it is to be noted that the instrument can also be implemented with no expander part 3 at all.

Inside the shaft 1 there is provided a cannula 7 extending from one end of the shaft to the other end thereof and enabling a control spike possibly needed in an operation to be conveyed into the drilled tunnel. The structure of the cannula 7 is known per se, so it will not be discussed in closer detail in the present application.

The use of the instrument will be described in closer detail in connection with FIG. 4.

Figure 4:
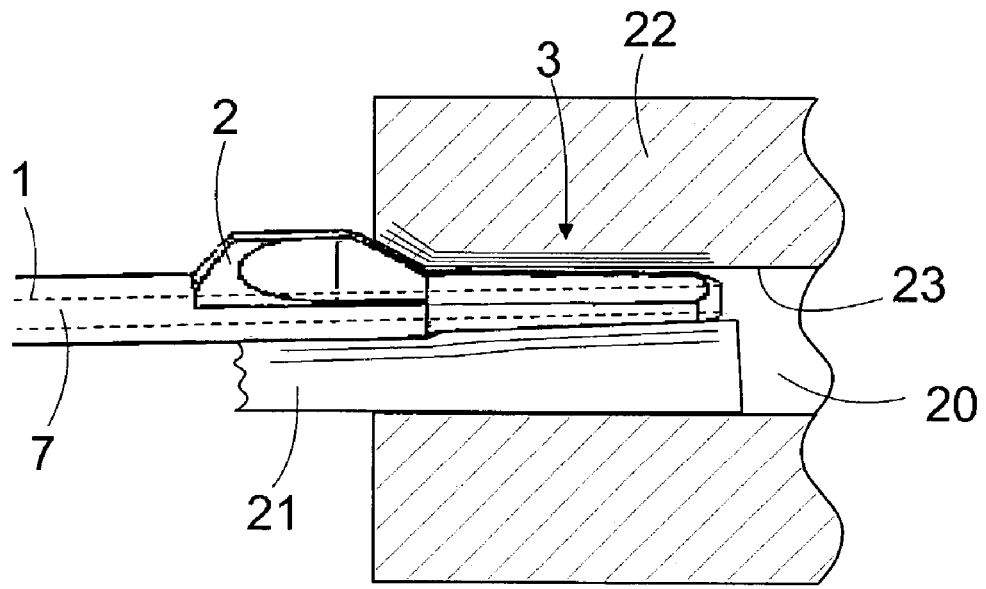
FIG. 4 is a schematic side view showing a first end of an instrument of the invention, partially inserted into a drilled tunnel.

FIG. 4 is a schematic side view showing a first end of an instrument of the invention, partially inserted into a drilled tunnel. The drilled tunnel 20 is provided in an end of a femur in a manner known per se, i.e. by drilling. A second end of a graft 21 is inserted into the drilled tunnel 20. Only a part of the graft 21 is shown in FIG. 4. Herein, the graft 21 is a soft tissue graft, shown in a strongly simplified manner, but the instrument can be used in any known tissue graft or artificial graft operations.

To be precise, the instrument is inserted between the graft 21 and a front wall 23 of the drilled tunnel 20. The diameter of the drilled tunnel 20 is sized according to the graft 21 and the screw used for fixing the graft 21.

The instrument is pushed into the drilled tunnel 20 such that the projection 2 is substantially outwards from the graft 21. Before the projection 2 comes into contact with a bone 22, the expander part 3 of the instrument packs the bone 22 and the end of the graft 21, which results in an increase of the diameter of the space between the graft and the front wall 23. Packing the graft 21 mainly means that the end of the graft residing in the drilled tunnel is subjected to flattening, compressing or the like. If the graft is a bone-tendon-bone graft, bone packing mainly means that the bone part of the graft residing in the drilled tunnel 20 is tightened.

When the projection 22 and the cutting edge 5 at the front edge thereof come into contact with the bone, the operator turns the instrument back and forth around the longitudinal axis A of the instrument. Typically, the extent of the turning movement is approximately 90° at most, which means that the operator is capable of carrying out such a movement by means of a wrist movement, without changing his or her grip on the instrument. If necessary, the turning movement may naturally be more extensive. During the turning movement, the cutting edge 5 of the blade cuts the bone 22 residing at the mouth part of the drilled tunnel, on the side facing the front wall. The cutting angle a of the cutting edge 5 determines the angle of a bevel being formed in the bone 22.

The blade 4 of the instrument modifies the mouth part of the drilled tunnel only on the side of the front wall 23. To no extent does the blade 4 modify the graft 21; neither does the graft 21 become subjected to considerable stresses during the turning movement. In particular, no cutting forces whatsoever are imposed on the graft since the blades 4 and the cutting edges 5 thereof do not come into contact with the graft 21 in any stage of the turning movement. Consequently, using the instrument enables the graft 21 to remain intact.

During the turning movement, the instrument gradually penetrates deeper into the drilled tunnel 20 while the expander part 3 simultaneously packs the bone 22 and the graft 21. The edges 6 of the expander part cut the bone 22 to some extent, which enhances the process of increasing the space between the graft 21 and the front edge 23 of the drilled tunnel. The edges 6 of the expander part are not sharp enough to in any way damage the graft 21. As already mentioned above, the expander part 3 does not necessarily include edges 6. The edges 6 and the number thereof may also be such that only the side of the expander part 3 coming into contact with the front wall 23 is provided with edges while the side coming into contact with the graft 21 has no edges at all.

In some operations, it is also possible to push the projection 2 of the instrument into the drilled tunnel 20, whereby the face 8 and the top 11 of the projection pack the bone 22 efficiently.

Inside the shaft 1 there is provided a cannula 7 having the same length as the shaft and a direction parallel with the longitudinal axis A. Both ends of he cannula 7 are open ends, enabling a control spike to be arranged through the shaft 1. The control spike may be used e.g. for directing the instrument in a correct position into the drilled tunnel 20; in such a case, the control spike is first conveyed into the drilled tunnel 20, between the graft 21 and the front wall 23, while a free end of the control spike is arranged through the cannula 7. Next, the instrument is inserted into the drilled tunnel 20 along the control spike. The control spike may be left in the drilled tunnel 20 after the drilled tunnel has been shaped using the instrument since the instrument can be removed from the operated area along the control spike. Next, the control spike can be used for directing a cannulated implant, such as a screw, into the drilled tunnel 20, or for another task known per se.

The cannula 7 may also be utilized for installing a control spike. In such a case, the instrument is first inserted into the drilled tunnel 20 and next, the control spike is conveyed through the cannula 7 into the drilled tunnel 20. The control spike is then used e.g. for directing a cannulated screw or other cannulated instruments into the drilled tunnel.

In the instrument shown in FIGS. 1 to 4, an expander part 3 and a cannula 7 have been connected to the instrument shaping the mouth part of the drilled tunnel. One and the same instrument can be used for several different working phases of the operation. This enables the number of instruments necessary for the operation to be reduced, which makes the operation simpler to perform. It is to be further emphasized in this connection that it is possible to implement the instrument with no expander part 3 and/or cannula 7.

Figure 5A:
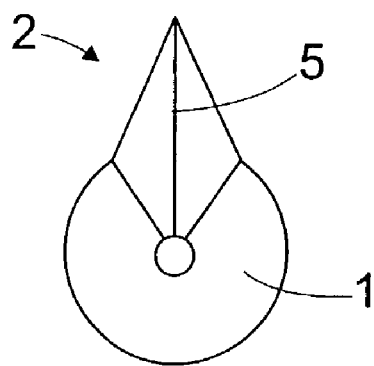
FIGS. 5a and 5b are schematic end views showing some instruments of the invention as seen from the direction of a first end.
Figure 5B:
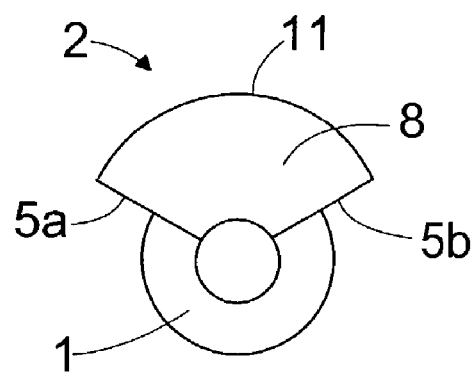

FIGS. 5a and 5b are schematic views showing some instruments of the invention as seen from the direction of a first end.

A projection 2 in the instrument shown in FIG. 5a includes only one blade 4 whose cutting edge 5 shapes by a turning movement taking place both in a first and a second turning direction. The edge 5 constitutes the face and the top of the projection. The instrument shapes the bone almost entirely by cutting; the instrument performs practically no bone packing at all.

The instrument shown in FIG. 5b is provided with two blades 4a, 4b having different directions. The angle between the blades is about 120°. The surface area of the face 8 and the top 11 of the projection 2 is very large, so the instrument packs the bone efficiently, particularly if the projection in its entirety is inserted into the drilled tunnel.

The projections 2 of the instrument shown in FIGS. 5a and 5b can be applied in connection with an expander part or with no such part.

The drawings and the related description are only intended to illustrate the idea of the invention. In its details, the invention may vary within the scope of the claims. The use of the instrument is thus not restricted to ACL/PCL operations but the instrument can also be used in other corresponding operations. Naturally, the first end 12 must be sized taking into account any requirement set by a particular operation. The instrument may also be used for modifying implants other than drilled tunnels for screws. The sizing and dimensions of the instruments shown in the figures are only given by way of example.

The invention claimed is:

1. An instrument for shaping a mouth part of a drilled tunnel provided in a bone, the instrument comprising a shaft having a longitudinal axis and a first and a second end and being hollow along its entire length, the first end of the shaft being provided with a projection, which includes two blades that are immobile with respect to the shaft for shaping the mouth part of the drilled tunnel when the instrument is turned around the longitudinal axis of the shaft, all of the blades on the projection being positioned on one side of a plane that divides the shaft into two halves, wherein the instrument is asymmetric at an intersecting surface perpendicular to the longitudinal axis and intersecting with the blade, and wherein the instrument shapes the surfaces surrounding the first end only substantially within an area corresponding with a turning angle of such a turning movement.

2. The instrument of claim 1, wherein the blades are mutually substantially parallel.

3. The instrument of claim 1, wherein the blades are mutually divergent.

4. The instrument of claim 1, wherein a cutting edge of each of the blades is concave.

5. The instrument of claim 1, wherein the cutting edge of each of the blades is straight.

6. The instrument of claim 1, wherein the first end is provided with an expander part such that the projection resides between the expander part and a tip of the second end.

7. The instrument of claim 6, wherein the expander part is provided with at least one cutting edge having a direction substantially parallel with the longitudinal axis.

8. The instrument of claim 6, wherein the diameter of the expander part diminishes towards a tip of the first end.

9. A use of the instrument of claim 1 in ACL/PCL operations comprising the following steps:
   drilling a tunnel into one of a femur or a tibia;
   inserting an end of a graft in the tunnel;
   inserting the first end of the shaft between the graft and a wall of the tunnel such that the projection extends substantially outward away from the graft; and
   turning the shaft back and forth about the longitudinal axis.

10. The use of the instrument of claim 9, further comprising the steps of:
- inserting a control spike into the tunnel before the step of inserting the first end of the shaft between the graft and the wall of the tunnel; and
- inserting the shaft along the control spike as the first end of the shaft is inserted between the graft and the wall of the tunnel.

11. The use of the instrument of claim 9, further comprising the steps of:
- inserting a control spike through the hollow shaft into the tunnel; and
- directing a cannulated instrument into the tunnel with the control spike.

* * * * *